United States Patent [19]
Guttag

[11] Patent Number: 5,648,084
[45] Date of Patent: Jul. 15, 1997

[54] MULTIPLE DOSAGE MEDICINE DROP BOTTLE

[76] Inventor: Alvin Guttag, Apt. 108, 415 Russell Ave., Gaithersburg, Md. 20877

[21] Appl. No.: 294,400

[22] Filed: Aug. 23, 1994

Related U.S. Application Data

[63] Continuation-in-part of Ser. No. 224,718, Apr. 8, 1994, which is a continuation-in-part of Ser. No. 853,428, Mar. 18, 1992, Pat. No. 5,346,929, which is a division of Ser. No. 486,217, Feb. 28, 1990, Pat. No. 5,120,089.

[51] Int. Cl.$^6$ .................................................. A61K 9/00
[52] U.S. Cl. .............................. 424/405; 424/400; 424/45
[58] Field of Search ............................ 424/400, 405, 424/401, 45, 248.4; 106/15.05; 426/237; 514/58

[56] References Cited

U.S. PATENT DOCUMENTS

| | | | |
|---|---|---|---|
| 3,767,790 | 10/1973 | Guttag | 424/81 |
| 3,970,530 | 7/1976 | Madlowski et al. | 426/237 |
| 4,419,352 | 12/1983 | Cox et al. | 424/248.4 |
| 4,514,225 | 4/1985 | Landsiedel | 106/15.05 |
| 5,232,687 | 8/1993 | Geimer | 424/45 |
| 5,324,718 | 6/1994 | Loftsson | 514/58 |
| 5,346,929 | 9/1994 | Guttag | 523/124 |

*Primary Examiner*—Thurman K. Page
*Assistant Examiner*—William E. Benston, Jr.
*Attorney, Agent, or Firm*—Cushman Darby & Cushman IP Group of Pillsbury Madison & Sutro, LLP

[57] ABSTRACT

The present invention reveals a multiple dosage medicine drop bottle or medicinal container having a germicide on at least the outside tip of the bottle or container. The present invention also reveals a method for reducing or eliminating the risk of contamination of the multiple dose medicine drop bottle or medicinal container and it contents. The bottle or container may also contain an aqueous solution of an anticlotting agent.

21 Claims, 1 Drawing Sheet

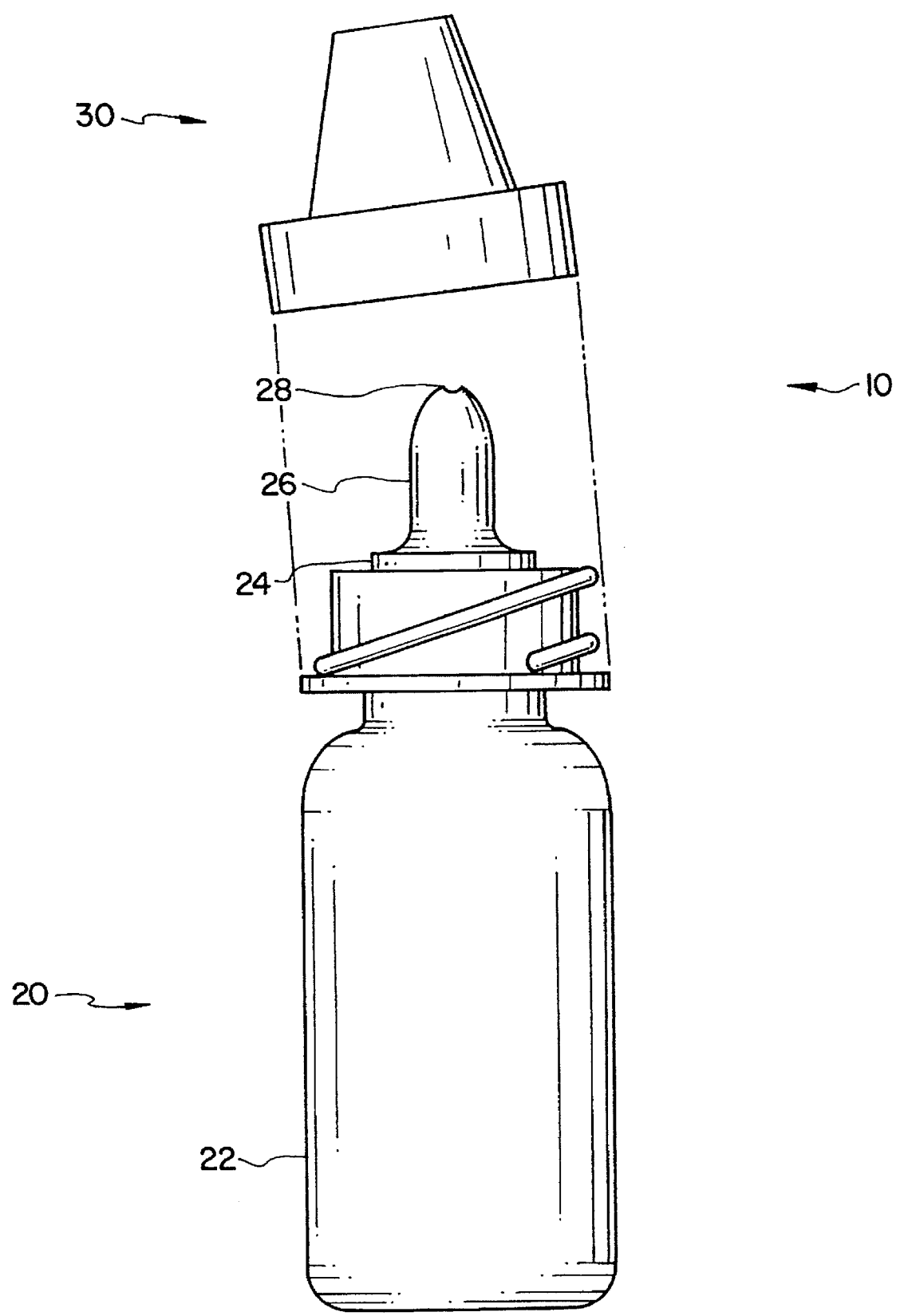

MULTIPLE DOSAGE MEDICINE DROP BOTTLE

This application is a continuation-in-part of U.S. patent application Ser. No. 08/224,718, filed Apr. 8, 1994, which is a continuation-in-part of U.S. patent application Ser. No. 07/853,428, filed Mar. 18, 1992, now U.S. Pat. No. 5,346,929, which is a division of U.S. patent application Ser. No. 07/486,217, filed Feb. 28, 1990, which issued as U.S. Pat. No. 5,120,089 on Jun. 9, 1992, the entire disclosures of which are hereby incorporated by reference and relied upon.

BACKGROUND OF THE INVENTION

1. Field of the Invention

The present invention relates to multiple dosage medicine drop bottle comprising a germicide and a method for reducing or eliminating the risk of contamination of the multiple dosage medicine drop bottle and its contents.

2. Description of the Related Art

TIMOPTIC® is the registered trademark for a sterile ophthalmic solution produced by Merck & Co., Inc., West Point, Pa. Each ml of TIMOPTIC® 0.25% contains 3.4 mg of timolol maleate (equivalent to 2.5 mg of timolol), monobasic and dibasic sodium phosphate, sodium hydroxide (to adjust pH), benzalkonium chloride 0.01% and water. TIMOPTIC® is also available as a 0.5% ophthalmic solution.

Timolol maleate is the active ingredient and benzalkonium chloride is added as a preservative. Timolol maleate is a non-selective beta-adrenergic receptor blocking agent. Its chemical name is (S)-1-[(1,1-dimethylethyl)amino]-3-[[4-(-morpholinyl)-1,2,5-thiadiazol-3-yl]oxy]-2-propanol, (Z)-2-butenedioate (1:1) salt.

The instructions accompanying the 10 and 15 ml OCU-METER® ophthalmic dispenser bottle for TIMOPTIC® ophthalmic solution states "To avoid contamination, be careful not to touch the dropper or let it touch your eye". The instruction pamphlet accompanying the 10 and 15 ml OCU-METER® bottle further states:

Patients should be instructed to avoid allowing the tip of the dispensing container to contact the eye or surrounding structures.

Patients should also be instructed that ocular solutions, if handled improperly, can become contaminated by common bacteria known to cause ocular infections. Serious damage to the eye and subsequent loss of vision may result from using contaminated solutions.

As a practical matter it is almost impossible with self-administered droppers, e.g., for eye drops, ear drops, nose drops, not to touch the body, e.g., the skin and/or eyelashes, the skin and/or otic hairs, the skin and/or nasal hairs, when using such droppers. With single dose dispensers, there is no serious problem with contamination. With containers designed for repeated dosages (such as 1, 5, 10 and 15 ml bottles), there is, however, the danger that microbes from the skin and hair will contaminate the bottle and/or solution as the result of the contact of the dropper end of the bottle with the skin and/or hair during the administration of the solution. The next time that the medicinal solution is administered, it may be contaminated with the undesirable microbes, e.g., bacteria, fungi.

The danger of contamination is further increased by the fact that the microorganisms will have time to multiply during the normal time lag between administering dosages. TIMOPTIC® Ophthalmic Solution is usually administered twice a day or every twelve hours. Under favorable conditions, many bacteria double every half hour. Thus, if any of the liquid from the dropper happens to remain on the area of the bottle which contacted the skin and/or hair of the eyes, ears or nose, the risk of undesirable microorganism growth is increased.

I have now found that this danger of contamination can be reduced or eliminated if the spout end of a multiple dosage medicine plastic bottle is provided with a germicide, e.g., a bactericide, fungicide or an oligodynamic metal.

In a second aspect of the present invention, a multiple dosage bottle can contain another medicine which is useful as an anti-clotting agent in addition to the eye, ears or nose drops.

SUMMARY OF THE INVENTION

One aspect of the present invention is for a multiple dosage medicine drop bottle or medicinal container having a germicide on at least the outside tip of the bottle or container. The germicide may be employed in the hydrophobic or hydrophilic synthetic resin of the bottle or container and may be, for example, a bactericide or a fungicide or both.

In another aspect of the present invention, the multiple dosage medicine drop bottle or medicinal container having a germicide contains eye drops, ear drops or nose drops as the medicine or medicinal solution.

In another aspect of the present invention, the multiple dosage medicine drop bottle or medicinal container having a germicide contains eyes drops, ear drops or nose drops and further contains a water soluble anticlotting agent.

Another aspect of the present invention is for a method for reducing the risk of contamination of a multiple dose medicine drop bottle or medicinal container and its contents by applying a medicinal solution from the bottle or container having a germicide on at least the tip of the bottle or container in which the bottle or container has previously been used to apply the medicinal solution.

In another aspect of the present invention for a method for reducing the risk of contamination of a multiple dose medicine drop bottle or medicinal container and its contents, the bottle or container further contains an aqueous solution of an anticlotting agent.

BRIEF DESCRIPTION OF THE DRAWING

The FIGURE graphically illustrates a multiple dose medicine drop bottle and its component parts. The multiple dosage medicine drop bottle 10 is comprised of a main body portion 20 and a gap 30. The main body portion 20 further comprises a relatively large diameter medicine reservoir portion 22 and a narrow dispensing or spout end 24. The dispensing or spout end 24 contains a tip 26 with a hole 28 at the distal end of the dispensing or spout end 24 for dispensing drops of medicinal solution. The medicinal solution is contained in the reservoir portion 22 of the bottle 10 and is delivered through the inside (not shown) of the spout end 24 to the hole 28 in the tip 26 for delivery to the target body part.

DETAILED DESCRIPTION OF THE PREFERRED EMBODIMENTS

The present invention discloses a multiple dosage plastic medicinal container 10 having a germicide on at least the outside of a tip 26, thereby reducing or eliminating the risk of contamination of the container 10 and its contents. The germicide may be comprised of a bactericide, a fungicide, an oligodynamic metal or any combination thereof.

While the entire outside of the bottle or container 10 can be treated with the germicide or germicides, this entire treatment is not normally necessary. The spout portion 24 of the bottle 10 is normally covered by a cap 30, e.g. a screw cap or a press-on cap, and usually it will be simplest to simply coat the portion of the bottle to be covered by the cap 30 with the germicide of the present invention.

In some cases treating the entire outside of the bottle or container 10 with the germicide or germicides is even undesirable. For example, if the germicide should be an irritant for the skin of the hands, it is best for the germicide not to be present in the area where the bottle 10 is handled. Thus, in a bottle 10 such as the OCUMETER®, the squeezable, flexible large diameter main portion 20 of the bottle 10 need not be treated but instead only the narrow spout end portion 24 which is designed to dispense one drop at a time.

The entire length of the spout 24, e.g. 10 to 15 mm, can be treated with the germicide or to reduce expense only the tip 26, e.g. the top 2-5 mm, need be treated. In some cases only the top 1 mm of the tip 26 need be treated. The germicide treated portion of the bottle 10 can be for the entire thickness of that portion of the bottle 10, e.g. the germicide portion of the bottle can be incorporated while molding the bottle 10 or the germicide portion can be incorporated later. For economical reasons and also if it is not desired for the germicide used to contact the inside of the bottle 10, then the germicide portion can be applied simply as an outer ply in forming a multi-ply bottle or can be applied as an outer coating after finishing the rest of the bottle.

The germicide or germicides can be applied in (or on) a hydrophobic plastic or in or on a hydrophilic plastic. The main portion 20 of the bottle 10 will normally be made of a hydrophobic plastic, e.g. an olefin polymer. The plastic can either be a synthetic resin or an elastomer.

Typical hydrophobic synthetic resin plastics include polymers such as those set forth in Guttag, U.S. Pat. No. 4,952,426 in column 2, lines 42-62 and column 3, lines 14-22, the entire disclosure of which is hereby incorporated by reference and relied upon. Illustrative elastomers include natural rubber, butadiene-styrene copolymer, butadiene-acrylonitrile copolymer and polychloroprene.

Typical hydrophilic synthetic resins include those set forth in Guttag, U.S. Pat. No. 3,633,546 in column 1, line 61 to column 3, line 32 and Guttag, U.S. Pat. No. 3,767,790 in column 3, line 13 to column 4, line 62, the entire disclosure of which is hereby incorporated by reference and relied upon.

The hydrophilic polymers permit the germicide to leach to the outside of the bottle 10 if any liquid from the drop being applied to the eye, ear or nose does not go into the target body part but instead remains on the bottle 10. This germicide leaching effect results in fresh germicide being applied to any microorganism on the outer surface of the bottle 10. The hydrophilic polymers are normally used only as an outer layer since their use on the inside of the bottle would result in the germicide leaching into the medicine or medicinal solution. In some case, the leaching of the germicide into the medicinal solution would be undesirable.

Sometimes when only the outside of the spout-drop dispenser 24 is treated with the germicide, it may also be desired to treat the inside of the tip 26 of the bottle 10 with the germicide to insure no contamination. Here again, there should be used a germicide which will not affect the medicine or medicinal solution, e.g. TIMOPTIC® 0.25%, inside the dropper 10. For example, the outside and the inside of the tip 26 of the bottle 10 can have a coating of metallic silver or gold.

It may also be desirable to include a germicide in the cap 30 of the bottle. The entire cap 30 may contain the germicide or the germicide may be limited to the inside of the cap 30. In some cases, it may be desirable to coat the inside of the cap 30, e.g. a screw cap, with a germicide, e.g. an organic germicide and/or an oligodynamic metal such as silver or gold, in addition to or in place of coating on the container itself. Thus, the germicide-containing cap 30 may be used in conjunction with or without a germicide-containing main body portion 20.

Furthermore, the inside of the cap 30 frequently is designed to touch the tip 26 of the bottle 10. Coating the inside of the cap 30 with the germicide will insure that the germicide contacts any liquid left after application of the medicine or medicinal solution.

Even in those cases where the medicinal solution contains a germicide, e.g. as a stabilizer, it is still important to treat the container 10, e.g. in the spout portion 24, according to the invention. There are several reasons for this. The amount of germicide in the portion of the medicinal solution left on the bottle 10 may not be sufficient to kill all of the bacteria or other microorganisms on the bottle or none of the medicinal solution may be left on the bottle. Furthermore, the spout 24 or tip 26 portion may be wet due to tears, sweat or water from other sources, thereby creating an ideal environment for unwanted microorganism growth even if no medicinal solution is left on the container 10.

Illustrative germicides include cetyl pyridinium chloride, Bactrin (a mixture of 160 mg trimethoprim and 800 mg of sulfamethoxazole), Cefobid (cefaperazone sodium), Neosporin (polymyxin B sulfate-neomycin sulfate), Betadine (povidone-iodine), Fungizone (Amphotericin B), Beconase (Bectomethasone dipropionate monohydrate), penicillin, oxytetracycline, streptomycin, erythromycin, bacitracin, tetracycline, gramicidin, tyrocidin, viomycin, aureomycin, neomycin. Examples of oligodynamic metals include silver and gold.

The following non-limiting examples are used to illustrate this aspect of the present invention. Unless otherwise indicated all parts and percentages are by weight.

EXAMPLE 1

In a typical example, a 10 ml OCUMETER® bottle 10 has the upper 5 mm of the tip 26 coated with molten polyethylene containing 10% by weight finely divided silver. The bottle 10 is then filled with TIMOPTIC® 0.25% ophthalmic solution.

EXAMPLE 2

A hydrophilic copolymer of 100 parts of 2-hydroxyethyl methacrylate and 0.5 part of ethylene glycol dimethacrylate saturated with cetyl pyridinium chloride was adhered as an external coating to the upper 2 mm of the tip 26 of the outside of an OCUMETER® bottle 10 containing TIMOPTIC® 0.5% ophthalmic solution.

EXAMPLE 3

A mixture of finely divided silver and Bactrin in an amount of 25% of the weight of the silver was applied as a coating to the upper 5 mm of the tip 26 of an OCUMETER® bottle 10 containing TIMOPTIC® 0.5% ophthalmic solution. The screw cap 30 was then screwed on the coated bottle 10.

While the Examples have been directed primarily to the use of TIMOPTIC®, it will be realized that there can be used any other beta-adrenergic receptor blocking agent suitable for reducing intraocular pressure whether or not accompanied by glaucoma. The invention is particularly well suited to the treatment of glaucoma or prevention of glaucoma by reducing intraocular pressure. The invention can also be used with other types of eye drops, e.g. 1, 2, 3 or 4% pilocarpine solutions or 0.5, 1 or 2% epinephrine hydrochloride solutions.

In a second aspect of the present invention, a multiple dosage bottle 10 can contain, in addition to the eye, ear or nose drops, another medicine which is useful as an anticlotting agent for blood. In this aspect of the invention, it is not essential to treat the bottle end and/or the bottle cap 30 with a germicide since this aspect of the invention is designed primarily to introduce an anticlotting agent simultaneously with the medicine in the eye, ear or nose drops. Since eye drops are normally administered once or twice a day, this is an ideal way to assure a small but relatively continuous dosage of the anticlotting agent since the anticlotting agent can be absorbed systemically as it is administered in the eye.

Aspirin is an example of an anticlotting agent and it is usually employed in relatively low dosages for its anticlotting action. As the anticlotting agent in place of aspirin, there can be used any of the other known medicinally active salts of acetylsalicylic acid, e.g. calcium aspirin or to use any of the aspirin substitutes which are the subject matter of U.S. patent application Ser. No. 08/224,718, the entire contents of which are hereby incorporated by reference and relied upon. Aspirin substitutes are represented by the following Formula I:

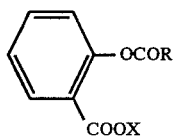

wherein R is an alkyl group (straight chain or branched chain) of 2 or more carbon atoms (advantageously, 2 to 17 carbon atoms) or an alkenyl group (straight chain or branched chain) of 2 to 23 carbon atoms, an aryl group (advantageously, phenyl), and X is hydrogen or a pharmaceutically acceptable salt forming metal or group (advantageously, sodium, potassium, lithium, calcium or ammonium salts).

It is preferable to employ the higher alkyl homologues of aspirin and the aryl and alkenyl homologues of aspirin in this aspect of the invention since they are more resistant to hydrolysis than is aspirin itself. Therefore, when aspirin substitutes are employed together with the other medication, e.g. a beta-adrenergic receptor blocking agent, the resulting medication will have a longer shelf life than if aspirin or calcium aspirin is employed. It is especially preferred to use as the medicine having aspirin-like properties, a compound of Formula I where R is an alkenyl group, especially an alkenyl group having 2 to 3 carbon atoms.

The anticlotting agent is also used as an inhibitor of platelet aggregation, see for example Sarnoff, U.S. Pat. No. 4,772,585, the entire disclosure of which is hereby incorporated by reference and relied upon. According to the second aspect of the invention, the eye drop bottle 10 can also include a protein thrombotic agent such as t-PA or streptokinase which can then be administered along with the eye medication.

The following non-limiting examples are used to illustrate this aspect of the present invention.

EXAMPLE 4

In illustrative examples according to the present invention, there can be employed:

(a) an aqueous solution containing 0.25% timolol maleate (as TIMOPTIC®) and 0.2% aspirin; or (b) an aqueous solution containing 0.25% timolol maleate and 5% calcium aspirin; or (c) an aqueous solution containing 0.5% timolol maleate (as TIMOPTIC®) and 0.2% of the sodium salt of methacryloyl salicylic acid; or (d) 0.25% timolol maleate and 5% of the calcium salt of acryloyl salicylic acid.

In each of Examples 4(a), 4(b), 4(c) and 4(d), the bottle employed can be a regular OCUMETER® bottle or an OCUMETER® bottle which has been treated in accordance with the first aspect of the invention, e.g. a 10 ml OCUMETER® bottle 10 having the upper 5 mm of the tip 26 coated with molten polyethylene containing 10% by weight finely divided silver or an OCUMETER® bottle 10 treated as described in Example 2 or Example 3 above.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

Thus, it is to be understood that variations in the multiple dosage medicine drop bottle can be made without departing from the novel aspects of this invention as defined in the claims.

What is claimed is:

1. A multiple dosage plastic medicinal container having an internal surface and an external surface and a relatively large diameter medicine reservoir portion terminating in a relatively narrow one drop dispensing end portion and a germicide on at least the external surface of said end portion.

2. The container according to claim 1 wherein said container contains a medicinal solution selected from the group consisting of eye drops, ear drops and nose drops.

3. The container according to claim 2 wherein said container contains eye drops.

4. The container according to claim 1 wherein said narrow one drop dispensing end portion has a tip portion, and said germicide is present only on the tip portion of said container.

5. The container according to claim 1 wherein said germicide is employed in a hydrophobic synthetic resin or elastomer.

6. The container according to claim 1 wherein said germicide is employed in a hydrophilic synthetic resin.

7. The container according to claim 1 wherein said germicide is a bactericide or fungicide.

8. The container according to claim 3 wherein said medicinal solution in said container further contains a water soluble anticlotting agent.

9. The container according to claim 8 wherein said anticlotting agent is a water soluble salt of acetylsalicylic acid or a water soluble salt of Formula I:

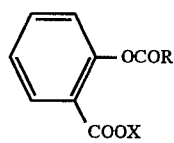

wherein R is an alkyl group of at least two carbon atoms, an alkenyl group of 2 to 23 carbon atoms or an aryl group; and X is a pharmaceutically acceptable salt forming group.

10. The container according to claim 9 wherein said eye medication is a beta-adrenergic receptor blocking agent.

11. A method for reducing the risk of contamination of a multiple dosage medicine drop bottle and its contents comprising:

applying a medicinal solution from a multiple dosage plastic medicinal container having an internal surface and an external surface and a relatively large diameter medicine reservoir portion terminating in a relatively narrow one drop dispensing end portion and a germicide on at least the external surface of said end portion which has previously been used to apply said medicinal solution.

12. The method of claim 11 wherein said bottle contains an aqueous solution of an anticlotting agent.

13. The method according to claim 12 wherein the anticlotting agent is a water soluble salt of acetylsalicylic acid or a water soluble salt of Formula I:

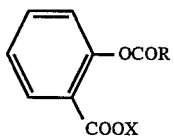

wherein R is an alkyl group of at least two carbon atoms, an alkenyl group of 2 to 23 carbon atoms or an aryl group; and X is a pharmaceutically acceptable salt forming group.

14. The method according to claim 13 further comprising administering said medicinal solution to the eye 1–2 times a day.

15. The container according to claim 1, wherein the germicide comprises an oligodynamic metal.

16. The container according to claim 15, wherein the germicide is employed in a hydrophobic synthetic resin or elastomer, or a hydrophilic synthetic resin.

17. The container according to claim 16, wherein the oligodynamic metal comprises silver and the germicide is employed in a hydrophilic resin.

18. The container according to claim 16, wherein the oligodynamic metal comprises silver and germicide is employed in a hydropholic synthetic resin or elastomer.

19. The container according to claim 2 wherein said medicinal solution in said container further contains a water soluble anticlotting agent which is a water soluble salt of Formula I:

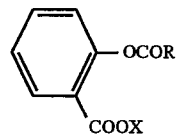

wherein R is an alkenyl group of 2 to 23 carbon atoms and X is a pharmaceutically acceptable salt forming group.

20. The container according to claim 15, wherein the oligodynamic metal is silver.

21. The container according to claim 15, wherein the oligodynamic metal is gold.

* * * * *

UNITED STATES PATENT AND TRADEMARK OFFICE
CERTIFICATE OF CORRECTION

PATENT NO. : 5,648,084
DATED : July 15, 1997
INVENTOR(S) : Alvin GUTTAG

It is certified that error appears in the above-identified patent and that said Letters Patent is hereby corrected as shown below:

Column 8, Line 17, replace "hydropholic" with --hydrophobic--.

Signed and Sealed this

Eighth Day of December, 1998

Attest:

BRUCE LEHMAN

Attesting Officer  Commissioner of Patents and Trademarks